(12) United States Patent
Schroeck et al.

(10) Patent No.: US 11,571,146 B2
(45) Date of Patent: Feb. 7, 2023

(54) ROTATION MONITORING SYSTEM AND METHOD

(71) Applicant: Cleveland State University, Cleveland, OH (US)

(72) Inventors: Christopher A. Schroeck, Erie, PA (US); Antonie J. van den Bogert, Cleveland Heights, OH (US)

(73) Assignee: CLEVELAND STATE UNIVERSITY, Cleveland, OH (US)

( * ) Notice: Subject to any disclaimer, the term of this patent is extended or adjusted under 35 U.S.C. 154(b) by 548 days.

(21) Appl. No.: 16/502,423

(22) Filed: Jul. 3, 2019

(65) Prior Publication Data
US 2020/0008715 A1 Jan. 9, 2020

Related U.S. Application Data

(60) Provisional application No. 62/693,467, filed on Jul. 3, 2018.

(51) Int. Cl.
*A61B 5/11* (2006.01)
*A61B 5/00* (2006.01)

(52) U.S. Cl.
CPC .......... *A61B 5/1121* (2013.01); *A61B 5/6828* (2013.01); *A61B 5/6831* (2013.01); *A61B 2562/0261* (2013.01)

(58) Field of Classification Search
CPC ... A61B 5/1121; A61B 5/6831; A61B 5/3828; A61B 5/6802; A61B 2562/219; A61B 2562/0261
See application file for complete search history.

(56) References Cited

U.S. PATENT DOCUMENTS

| | | | | |
|---|---|---|---|---|
| 2009/0306485 | A1* | 12/2009 | Bell | A61B 5/6839 600/301 |
| 2016/0242646 | A1* | 8/2016 | Obma | A61B 5/0024 |
| 2017/0231566 | A1* | 8/2017 | Klimek | A61B 5/6802 600/324 |
| 2017/0367594 | A1* | 12/2017 | Gu | A61B 5/11 |

(Continued)

FOREIGN PATENT DOCUMENTS

WO    WO-2015177749 A1 * 11/2015    ........... A61B 5/1126

OTHER PUBLICATIONS

Huang B, Li M, Mei T, et al. Wearable Stretch Sensors for Motion Measurement of the Wrist Joint Based on Dielectric Elastomers. Sensors (Basel). 2017;17(12):2708. Published Nov. 23, 2017. doi:10.3390/s17122708 (Year: 2017).*

(Continued)

*Primary Examiner* — Sean P Dougherty
*Assistant Examiner* — Alexander H Connor
(74) *Attorney, Agent, or Firm* — Lippes Mathias LLP

(57) ABSTRACT

A rotation monitoring system may be attached to a limb and can identify ranges of motion that are associated with injuries or poor performance. In some embodiments, the device is designed to monitor flexion and orientation of joints and limbs, developed specifically around identifying stress concentrating behavior on the ACL. Tests performed show that the designed device can read flexion and orientation of the knee, is durable enough to be used in real-world conditions, and does not impede on the subject's movements.

19 Claims, 13 Drawing Sheets

(56) References Cited

U.S. PATENT DOCUMENTS

2018/0271409 A1* 9/2018 Gong .................. A61B 5/1118

OTHER PUBLICATIONS

Pettys-Baker; Robert. Design and Development of Valgus-Sensing Leggings. Proceedings of the 2017 Design of Medical Devices Conference Apr. 10-13, 2017, Minneapolis, Minnesota, USA (Year: 2017).*

Yiğit Mengüç, Yong-Lae Park, Hao Pei, Daniel Vogt, Patrick M. Aubin, Ethan Winchell, Lowell Fluke, Leia Stirling, Robert J. Wood, and Conor J. Walsh. "Wearable soft sensing suit for human gait measurement." The International Journal of Robotics Research. Dec. 2014; 33(14): 1748-1764. (Year: 2014).*

* cited by examiner

ROTATION MONITORING SYSTEM AND METHOD

The present application claims priority to U.S. provisional patent application Ser. No. 62/693,467, filed Jul. 3, 2018, which is incorporated by reference herein in its entirety.

BACKGROUND

Preventable injuries in sports and physical activities are often caused by improper form. By some estimates, about 50-70% of all athletic injuries in college sports are preventable.

Recovery is often sub-optimal because many patients do not fully follow at-home exercises recommended by trainers and physical therapists.

Strain is the mechanical phenomenon of the relative deformation of a continuum in response to an applied force that obeys Hooke's Law. A continuum is a material with uniform, but not necessarily constant, properties. Strain sensors have been used for decades to measure deformations in rigid continuums (e.g. metals and ceramics) by being attached to the surface of said continuum and experiencing the deformation of that surface. This deformation mechanically distorts electrically active portions of the sensor, changing the sensor's interaction with an electrical signal in a way that is directly proportional to the strain experienced by the sensor. The deformation in the strain sensor can be equated to that in the continuum because the strain sensor and the continuum are elastic materials placed in parallel relative to the applied force, meaning they must share a similar deformation.

With advances in elastomer materials (highly elastic polymers), strain sensors have become less rigid, can move similarly to non-rigid continuums (e.g. skin and cloth), and can be made to double in size or more, but these nonrigid sensors can only make meaningful measurements while they are taut. The development of a soft, strain sensing monitor has led to an interest in the measurement of joint rotations on living bodies, particularly human bodies. Doing so entails using a strain sensor to monitor the deformation in an area of skin and attributing said deformation to the angular change experienced in a joint. This has been accomplished with rotations orthogonal to the axial direction of limbs and the spine (including, but not limited to, flexion/extension and abduction/adduction). The axial direction refers to the distal/proximal direction of limbs or the superior/inferior direction for the spine. A typical arrangement of a one degree of freedom (DOF) monitor like this would entail the attachment of a strain sensor to both ends of a synovial joint for the limbs (or one end near the pelvis and the other near either the sternum, C7 protuberance, or axillary region for the spine) to measure the deformation of the skin overlaying the joint(s) of interest. This displacement is correlated to the angular change experienced in the joint(s) of interest.

A better way for trainers/coaches to monitor their subjects is needed for safer and more effective results.

BRIEF DESCRIPTION

The present disclosure relates to systems and methods for monitoring rotation. The system may be attached to a limb and can identify ranges of motion that are associated with injuries or poor performance to a sufficient degree to allow injury and poor performance linked movements to be identified. In some embodiments, the system is designed to monitor flexion and orientation of joints and limbs. In other embodiments, the system is configured to identify stress concentrating behavior on the anterior cruciate ligament (ACL). Tests performed show that the system can be configured to monitor flexion, abduction, and rotational orientation of the knee, is durable enough to be used in real-world and athletic conditions and does not impede on the movement of a subject wearing the device.

Disclosed, in some embodiments, is a system for measuring axial rotational motion of a rigid body. The system includes a first anchor configured to be anchored at or near a proximal location which originates the rotational motion of a rigid body; a first strain-monitoring sensor connected to the first anchor; and a second anchor connected to the first strain-monitoring sensor and configured to be anchored on a distal location of the rigid body away from the first anchor.

In some embodiments, the first strain-monitoring sensor extends at least partially around an axis of rotation of the rigid body.

The system may further include a first strap connecting the first anchor to the first strain-monitoring sensor; and a second strap connecting the second anchor to the first strain-monitoring sensor.

In some embodiments, the sensor includes a polymer film sandwiched between two electrodes The system may further include at least one secondary strain-monitoring sensor configured to measure flexion of a hinge joint associated with the rigid body or abduction or flexion of a ball and socket joint associated with the rigid body.

Disclosed, in other embodiments, is a garment including a first system for measuring axial rotational motion of a rigid body. The system includes a first anchor configured to be anchored at or near a proximal location which originates the rotational motion of a rigid body; a first strain-monitoring sensor connected to the first anchoring element; and a second anchor connected to the first strain-monitoring sensor and configured to be anchored on a distal of the rigid body opposite the first anchor.

In some embodiments, the garment is pants; the rigid body is a femur; the proximal location is near a hip joint; and the distal location is near a knee joint.

The proximal location may be located on an upper area of a thigh; and the distal location may be located on a lower area of a thigh.

In some embodiments, both the proximal location and the distal location are located on a lateral face of the thigh.

In other embodiments, the garment is pants; the rigid body is a tibia and a fibula; the proximal location is near a knee joint; and the distal location is near an ankle joint.

In further embodiments, the garment is a long-sleeve shirt; the rigid body is a humerus; the proximal location is near a shoulder joint; and the distal location is near an elbow joint.

In other embodiments, the garment is a long-sleeve shirt; the rigid body is a radius and an ulna; the proximal location is near an elbow joint; and the distal location is near a wrist joint.

The garment may further include a second system for measuring flexion, the second system including a third anchor configured to be anchored on a first side of a hinge joint; a fourth anchor configured to be anchored on a second side of the hinge joint; and a sensor attached to the third anchor and the fourth anchor.

The hinge joint may be a knee joint or an ankle joint.

Disclosed, in further embodiments, is a method for measuring axial rotational motion of a rigid body. The method includes providing a system to a human, a non-human animal, or a machine; and measuring rotational motion with the system. The system includes a first anchor configured to be anchored at or near a proximal location which originates the rotational motion of a rigid body; a first strain-monitoring sensor connected to the first anchor; and a second anchor connected to the first strain-monitoring sensor and configured to be anchored on a distal location of the rigid body away from the first anchor.

The rigid body may be selected from a femur, a humerus, a tibia and a fibula, and a radius and an ulna.

In some embodiments, the method further includes assessing an injury risk based on the rotational motion measurement.

The injury may be selected from a torn anterior cruciate ligament (ACL), a torn ulnar collateral ligament (UCL), and shin splints.

In some embodiments, the system further includes a third anchor configured to be anchored on a first side of a hinge; a fourth anchor configured to be anchored on a second side of the hinge; and a second strain-monitoring sensor between the third anchor and the fourth anchor. The measuring of rotational motion within the system includes measuring a first strain from the first sensor; measuring a second strain from the second sensor; and using the second strain to remove pollution caused by flexion of the hinge and calculate a more accurate first strain.

DETAILED DESCRIPTION

Figure 1:
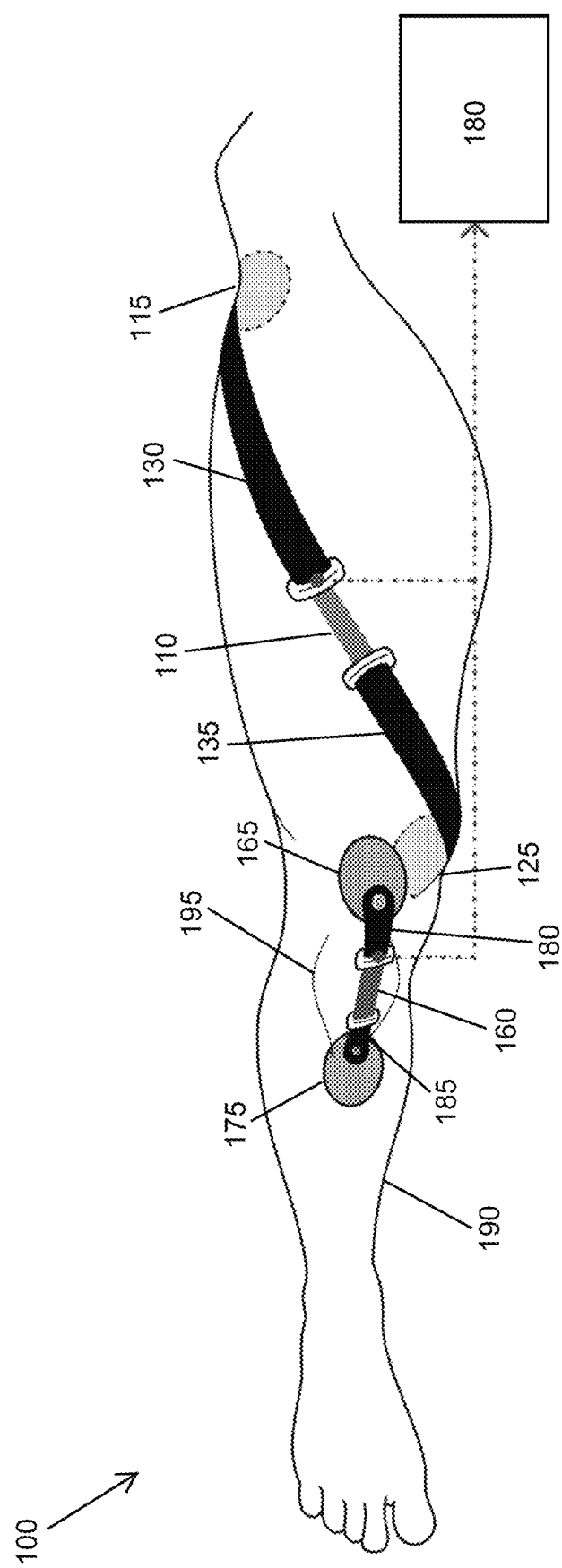
FIG. 1 is a perspective view of a monitoring system in accordance with some embodiments of the present disclosure.

The present disclosure may be understood more readily by reference to the following detailed description of desired embodiments included therein. In the following specification and the claims which follow, reference will be made to a number of terms which shall be defined to have the following meanings.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent can be used in practice or testing of the present disclosure. All publications, patent applications, patents, and other references mentioned herein are incorporated by reference in their entirety. The materials, methods, and articles disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases that require the presence of the named ingredients/steps and permit the presence of other ingredients/steps. However, such description should be construed as also describing compositions, mixtures, or processes as "consisting of" and "consisting essentially of" the enumerated ingredients/steps, which allows the presence of only the named ingredients/steps, along with any impurities that might result therefrom, and excludes other ingredients/steps.

Unless indicated to the contrary, the numerical values in the specification should be understood to include numerical values which are the same when reduced to the same number of significant figures and numerical values which differ from the stated value by less than the experimental error of the conventional measurement technique of the type used to determine the particular value.

All ranges disclosed herein are inclusive of the recited endpoint and independently combinable (for example, the range of "from 2 to 10" is inclusive of the endpoints, 2 and 10, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

If the correlation of the skin deformation is solely attributed to one joint, or a set of dynamically linked joints (e.g. the vertebrae in the spine), then the assumption is made that either the strain sensor is measuring the motion of the bones, directly, or the skin deformation is solely caused by the rotation of the joint being monitored. Strain sensors that attach to the skin and not directly to the bone will not directly measure the underlaying bone's motion, but the skin's deformation. The skin is an elastic continuum, spanning multiple joints that move independently from one another, some of which have multiple DOF. These local rotations will cause the skin to stretch and relax in a complex pattern that can accommodate each DOF it encompasses. Additionally, the skin is overlaying muscle bellies, which flex and relax relative to the rotations they cause and not necessarily relative to the rotation of a nearby joint. For example, the hip is capable of rotating the femur in three unique ways (flexion/extension, abduction/adduction, and internal/external rotation). Additionally, the groups of muscles known as the quadriceps (quads) and hamstrings (hamies) cause rotations in both the hip joint and the knee joint. To accurately correlate the observed skin deformations to any one DOF of the underlying femur, several, if not all, of the other DOFs of the hip and knee would need to be referenced to filter out any skin or muscular deformations not directly related to the DOF being monitored. A way around this excess deformation filtering is to constrain the hip to one DOF. Typically, this one DOF is flexion, allowing for two-dimensional gait analysis. For this to be a successful method, the gait being analyzed would need to be very cyclical, with constant hip abduction/adduction and internal/external rotation values.

For three-dimensional analysis via strain sensors, the axial joint rotation of long bones and the spine is needed for both its contributions to skeletal motions and the filtering of DOF non-specific skin and muscle deformations. Currently, there is no such method being used. This is due to the fact that the axial rotational motion of joints is difficult to measure directly, compared to the joint rotations orthogonal to the axial direction (e.g. flexion/extension, abduction/adduction). These orthogonal rotations have clearly defined reference areas proximal and distal to the originating joint. Joints which originate axial rotation typically produce rotations in all planes (e.g. the hip) or are located close enough to other joints to be topically affected by their motions (e.g. the proximal radioulnar articulation to the elbow, often assumed as one joint in human motion). Typical magnitudes of axial rotation are low, including the joint rotation and associated skin deformation, compared to typical flexion/extension and abduction/adduction magnitudes (e.g. typical shoulder motions). This becomes problematic for monitoring axial rotation because the axial rotational deformation may be small compared to the other rotation's deformations, making the signal before filtering non-representative of the motion and too small to be successfully calibrated after. Additionally, the anatomy around ball and socket joints restricts access to useful attachment areas. A useful attachment area is one that is out of the lines of motion of other body parts, that keeps the sensor taut in all positions being monitored, that keeps the sensor in contact with the surface of the body (if unsecured), and that produces stable, repetitious deformations that correspond to kinematically relevant joint rotations.

One strain sensor typically monitors one DOF. Measuring multiple DOFs with a single sensor would cause an interdependency between the measurements of deformations that are not interdependent. This is due to strain sensors being three-dimensional objects that obey Hooke's Law: when one dimension of an elastic object is deformed by a mechanical force, the other dimensions deform in a related, inverse way. Generally, the volume of the solid is considered constant unless otherwise noted. This deformation changes the sensors effects on an electrical signal, which is attributed fully to said unknown force. When multiple unknown forces are present, the sensor does not have enough information to determine the strain effects due to each unknown force. Even when multiple one DOF strain sensors are layered together in perpendicular directions, these sensors will either be in series or in parallel with one another, causing them to share forces and deformations. If multiple DOFs are to be monitored, an equal number of one-dimensional strain sensors or a multi-dimensional strain sensor with one less than the number of DOFs of one-dimensional force sensors would be needed to create a successful monitor. In both cases, the same number of sensors are needed.

The present disclosure relates to a system for monitoring rotation including a rotation sensor. The rotation sensor may include a non-rigid, strain or deformation-based sensor that can be anchored at or near the proximal the location which originates the rotational motion of the rigid body being observed, optionally crosses the rigid body, and is anchored to the opposite side of the same rigid body. The second anchor may be located at a distal region of the same solid body as the first anchor in an area that balances sensor response and pollution levels of non-relevant motions. The terms "anchor", "anchored", and the like refer to attachment points of the system to the body being measured. The anchor may be a separate element or may refer to an end of a strap or a sensor.

The sensors used herein may be length-monitoring sensors (e.g. strain-monitoring sensors).

The present disclosure also relates to a system for monitoring flexion using a flexion sensor. The flexion sensor may include a non-rigid, strain or deformation-based sensor that can be anchored to opposite, rigid areas surrounding a joint (which originates the flexion/extension or adduction/abduction) in order to isolate and observe the motion.

The present disclosure further relates to a system for monitoring rotation. The system may include both a rotation sensor and a flexion sensor as described above. The system may be used to monitor anatomical internal/external rotation (axial rotational motion of a limb or solid body).

FIG. 1 illustrates a system 100 including both a flexion sensor and a rotation sensor applied to a human leg. However, it should be understood that the flexion sensor is omitted in some embodiments. Additionally, more than one rotation sensor and/or more than one flexion sensor may be included in other embodiments. Furthermore, one or more abduction/adduction sensors/monitors may be included in addition or as an alternative to the flexion sensor(s). In the depicted system 100, the flexion and extension monitor 160 is secured to the leg 190 using anchors 165, 175 applied above and below the knee joint 195. In some embodiments, the anchors 165, 175 are chemically applied (e.g. via an adhesive directly to the skin). In other embodiments, the anchors 165, 175 are mechanically applied (e.g. via a band, athletic tape, or a sleeve extending at least partially around the leg). In further embodiments, the anchors 165, 175 may be applied via suction. A first strap 180 may be used to secure the sensor/monitor 160 to the first anchor 165 and a second strap 185 may be used to secure the sensor/monitor 160 to the second anchor 175.

The rotation monitor 110 is also secured to the leg 190 using anchors 115, 125. In the depicted embodiment, the anchors 115, 125 are applied such that the monitor 110 partially wraps around the leg 190. The rotation monitor anchors 115, 125 may have similar or different configurations compared to the flexion monitor anchors 165, 175. The rotation monitor 110 may be secured to the rotation monitor anchors 115, 125 via straps 130, 135.

Sensor measurements (e.g. voltages) are transmitted for data processing 180 (e.g. by a computer including a processor). Data transmission may be wired or wireless. In some embodiments, the data processing 180 is performed in real-time. In other embodiments, data is collected and subsequently processed at a later time. Data processing may be performed on-site or off-site.

In some embodiments, data collected from the same subject (e.g. patient and/or athlete) at different times is stored and analyzed. The analysis of changes in the data may be used, for example, to track performance progression or recovery from an injury.

In some embodiments, the anchor is an adhesive and/or gel-based anchor.

In some embodiments, the anchor includes tape (e.g. kinesiology tape).

The anchor may be sewn into a substrate (e.g. clothing). Clothing provides a consistent, easy to use setup. The clothing is optionally made from a high-friction cloth to reduce movement to the skin.

In non-limiting embodiments, the straps include a polymer (e.g. a polyamide). The polyamide may be based on an aliphatic or semi-aromatic polyamide such as Nylon. In other non-limiting embodiments, the straps contain a blend of a polyether-polyurea copolymer (e.g. Spandex or Lycra) and cotton. The anchors and/or clothing may also be made from these materials in some embodiments.

In clothing embodiments, the straps may be a fabric that deforms less or similarly to the rest of the garment. It is also possible to use a single strap or no straps.

The sensor(s) may be located within the fabric itself or attached to an interior or exterior surface thereof.

The sensor(s) may be any soft strain sensor(s) and may include a polymer film sandwiched between two electrodes in some embodiments. Deformation effects the electrical signal in a predictable, consistent manner (e.g. by increasing capacitance. The sensor(s) may be used to sense strain (i.e. the sensor's change in length). The sensor(s) may include an electroactive polymer. The electroactive polymer and/or components including the same may be as described in one or more of U.S. Pat. Nos. 7,733,575; 7,952,261; 8,950,265; and 9,394,896; and U.S. Pub. No. 2017/0279031. The contents of these documents are incorporated by reference herein in their entireties. In particular embodiments, the electroactive polymer is a dielectric electroactive polymer. Non-limiting examples of sensors include those sold by Parker Hannifin under the name FlexSense. However, other types of sensors are also contemplated.

The polymer film may be a silicon-based laminate.

The electrodes may be made from a conductive ink (e.g. graphite).

In some embodiments, the sensor(s) is/are soft, elastic strain sensor(s) that operate in low forcing loads.

The design of the pants may offer a similar pressure to athletes as kinesiology tape. In some embodiments, tension may be adjusted via one or more adjustable straps. In some embodiments, one or more additional sensors can be included to measure breathing rate, limb length(s), limb thickness(es), and/or injury-based movements (e.g. knee bending the wrong direction).

When the monitoring system is included in a garment, the garment may be selected from pants, shorts, shirts, and combinations thereof. The pants may be used to monitor rotation about a femur and/or a tibia and fibula. For example, the pants may include a rotation sensor located on the upper leg to measure rotation about a longitudinal axis of the femur. Similarly, the pants may include a rotation sensor located on the lower leg to measure rotation about a longitudinal axis of a tibia and a fibula. In some embodiments, the pants include both an upper leg rotation sensor and a lower leg rotation sensor.

The shirt may be used to monitor rotation about a humerus and/or a radius and an ulna. For example, the shirt may include a rotation sensor located on the upper arm to measure rotation about a longitudinal axis of the humerus. Similarly, the shirt may include a rotation sensor located on the lower arm to measure rotation about a longitudinal axis of the radius and ulna. In some embodiments, the shirt includes both an upper arm rotation sensor and a lower arm rotation sensor.

Shirts and pants may be combined into the same monitoring system. Alternatively, a bodysuit is also contemplated.

It should also be understood that additional sensors may be included such as flexion sensors (e.g. for measuring flexion/extension of hinge joints such as the knee and elbow) and/or abduction sensors (e.g. for measuring abduction/adduction of ball and socket joints such as the hips and shoulders).

Optionally, the rotation sensors of the present disclosure may cross the rigid body in a right-to-left or left-to-right manner and/or relative to an axis of rotation of the rigid body in order to magnify deformation and thus the signal (e.g. voltage signal) generated by the rotation. The rotation sensors may extend partially or completely around a longitudinal axis of the rigid body.

Figure 2:
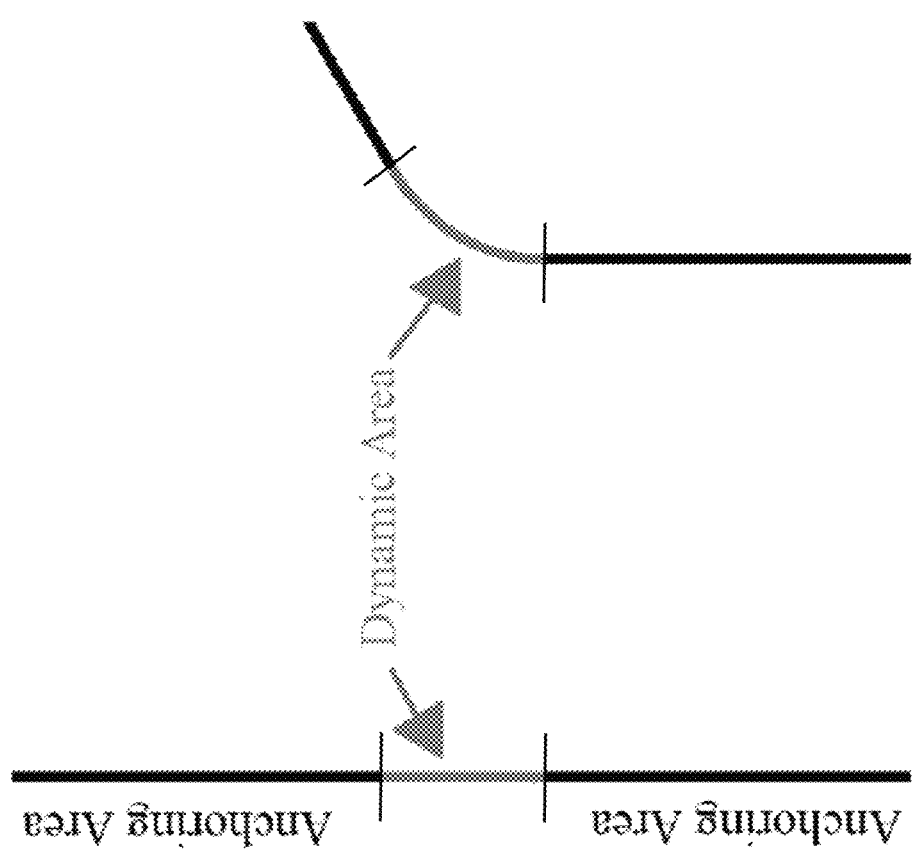
FIG. 2 is an illustration of the dynamic area and anchoring areas which can be enveloped by the anchors for a flexion sensor in accordance with some embodiments of the present disclosure.

FIG. 2 is an illustration of the dynamic area and anchoring areas for a flexion sensor in accordance with some embodiments of the present disclosure. For example, as a knee or elbow bends, the skin around it moves. The dynamic area represents the skin that moves the most because of the knee or elbow bending, while the other areas represent skin that does not notably move. FIG. 2 models a hinge joint (one that does only flexion and extension, in the depicted case the knee). The flexion sensor is a non-rigid, strain or deformation-based sensor that is anchored to opposite, rigid areas surrounding a joint which originates the flexion/extension, in order to isolate and observe the motion.

The dynamic area is not the only source of pollution, but it must be encompassed by the anchors to fully capture the joint movement. Other pollutants (not shown in FIG. 2) will exist around the joint due to muscular flexion/relaxation, skin motion, and close-by joint movements.

Any arrangement that positions itself otherwise would be more prone to pollution from outside pollution because they will be capturing a small amount of the total motion being monitored, thus making the claim to be a flexion sensor somewhat nonsensical. Knowing that these constraints must be observed and knowing that the calibration must make the motions observable in a meaningful (and unique) way helps to focus the development of the calibration and helps to avoid focusing on unimportant functions that are not essential for a flexion sensor.

Figure 3:
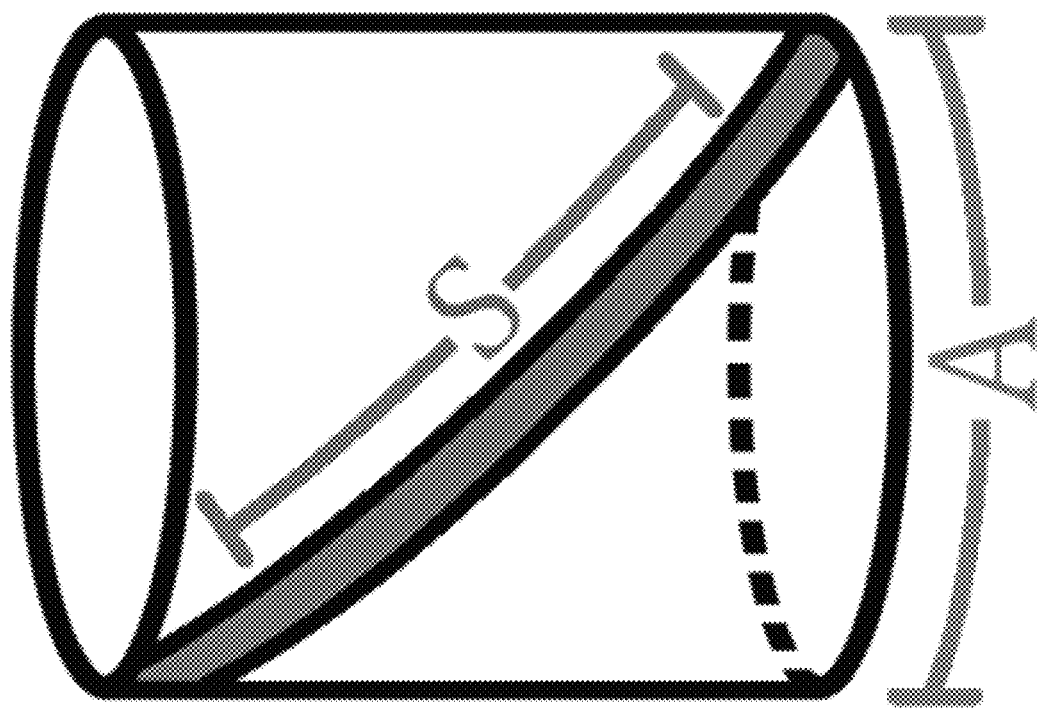
FIG. 3 is a geometric model of a rotation sensor arrangement on a rigid limb (e.g. a thigh) in accordance with some embodiments of the present disclosure.

FIG. 3 is a geometric model of a rotation sensor arrangement in accordance with some embodiments of the present disclosure. The geometric equation for the rotation sensor on the thigh is based on the physical design of the sensor layout. The modelling of the thigh's shape is simplified down to a cylinder, partly to help make the model easier, but also to act as a mean value of the dynamic shapes that an active thigh can take. However, a three-dimensional shape is much more difficult to work with than a two-dimensional shape. Since the only part of the cylinder that is of concern is the surface, the cylinder can be "unrolled" into a flat, two-dimensional plane without losing any of its value as a model. These assumptions can be made more reflective of reality by only using non-rigid sensors, by reducing the mass of the sensor-anchor system as much as possible, and by threading the sensor through a sheath or a type of belt loops that follow its path.

Figure 4:
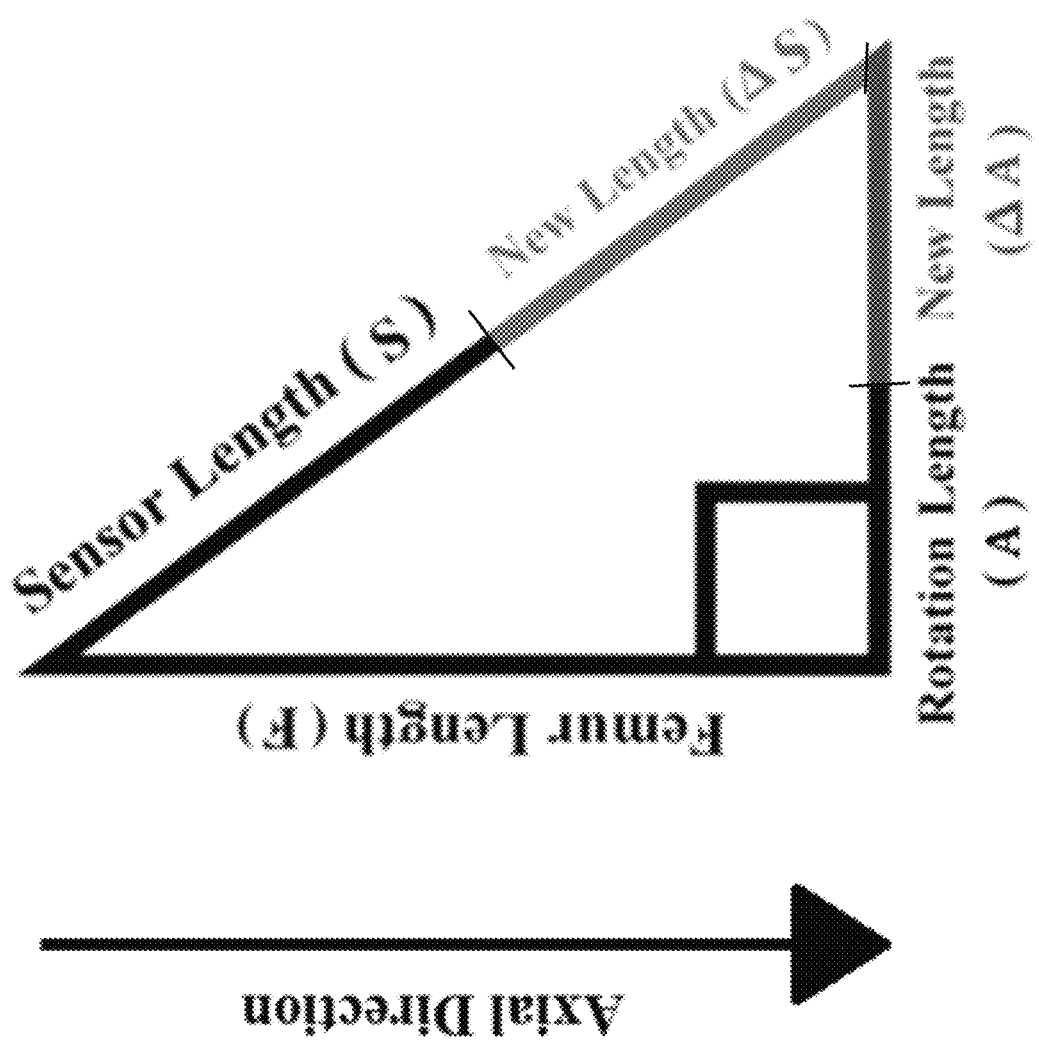
FIG. 4 is a graph illustrating a planar model of a correct, single rigid body rotation sensor setup with one unknown in accordance with some embodiments of the present disclosure.
Figure 5:
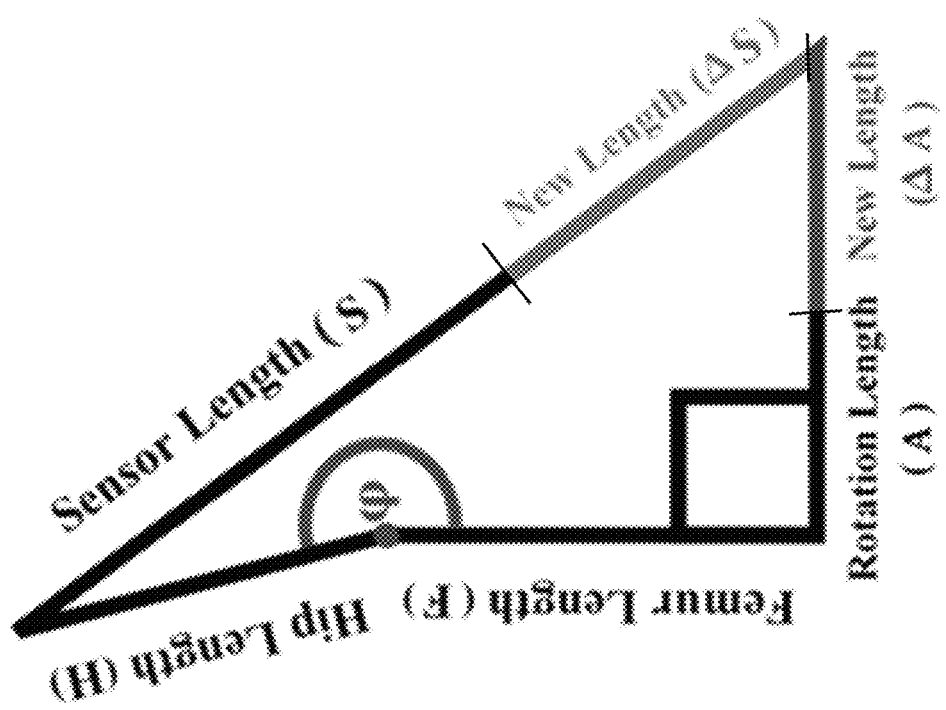
FIG. 5 is a graph illustrating a planar model of a sensor setup illustrating the issue where multiple unknowns become present when measuring across multiple rigid bodies requiring more sensor input.

FIG. 4 is a planar model of a correct, single rigid body (femur) rotation sensor setup with one unknown ($\Delta A$). FIG. 5 is a model with multiple unknowns (which cannot be solved for) with multiple rigid bodies. Here, the hip is a non-limiting example.

The accuracy of rotation sensors is more sensitive to proper anchoring locations than flexion sensors. One major principle of the rotation sensor is that the actual sensor is measuring the change in hypotenuse of a right triangle. With one side staying constant (which is why the arrangement stays on a single rigid body) and another's length change being measured, the desired measurement is the only unknown side of the triangle. This relation allows for a very basic trigonometric relation between the sensor data and the desired measurement. But for this relation to be valid, it is vital that the sensor be anchored only to the rigid body it is measuring, otherwise the shape will no longer be a right triangle with one unknown but a non-regular quadrilateral with two unknowns.

This is at first counter-intuitive because measuring the rotation of a rigid body with no external reference shouldn't be possible. Since the anchors are attaching to the skin and not the bone, the sensor is actually monitoring the motions of the skin and not the direct motion of the underlying bones. The skin, if healthy, is a continuum that bridges joints throughout their entire range of motion. Because skin on a rotating body needs to maintain its connection with skin not rotating, the topical motion will form a motion gradient close to the joint (this is the dynamic region), approaching no rotation at the joint location. This phenomenon offers specific areas of skin to be both a rotational reference point and a fixed axial distance from the point of measure. While this point is very mechanical, it is an essential concept for developing a calibration for this type of motion.

While crossing the rigid body is not necessary for basic function, it may offer a sort of magnifying effect to the deformation being observed. If this is neglected, the signal change may not be robust enough to uniquely define each possible position of rotation, but the calibration principles and trigonometric relationships will be the same. The geometric relation should follow the Pythagorean Theorem.

Figure 6:
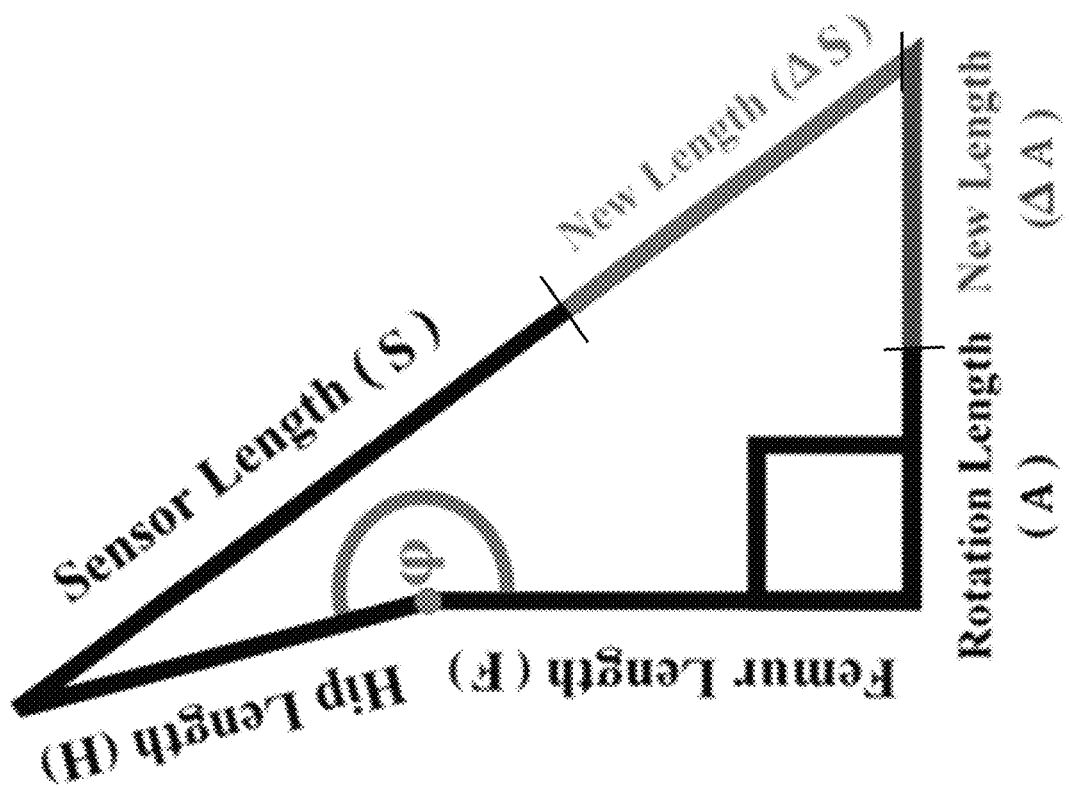
FIG. 6 is a planar explanation of a correct, multiple rigid body rotation sensor setup with one unknown, which uses flexion/abduction sensor data to determine variable angle $\psi$ in accordance with some embodiments of the present disclosure.

A combine data rotation (CDR) sensor is a rotation sensor that has its proximal anchor located on a separate rigid body—one that is isolated from the rotational motion. The device then uses corresponding joint sensor data to isolate the rotation data as the only unknown variable. FIG. 6 is a planar explanation of a correct, multiple rigid body rotation sensor setup with one unknown ($\Delta A$), which uses flexion sensor data to determine variable angle $\psi$. The hip is used as an example, meaning angle $\psi$ is a multi-dimensional angle.

A double combine data rotation sensor is a combine rotation sensor that has its non-proximal anchor on a separate rigid body—one that is not isolated from the rotational motion—and then uses corresponding joint sensor data to isolate the rotation data as the only unknown variable.

Figure 7:
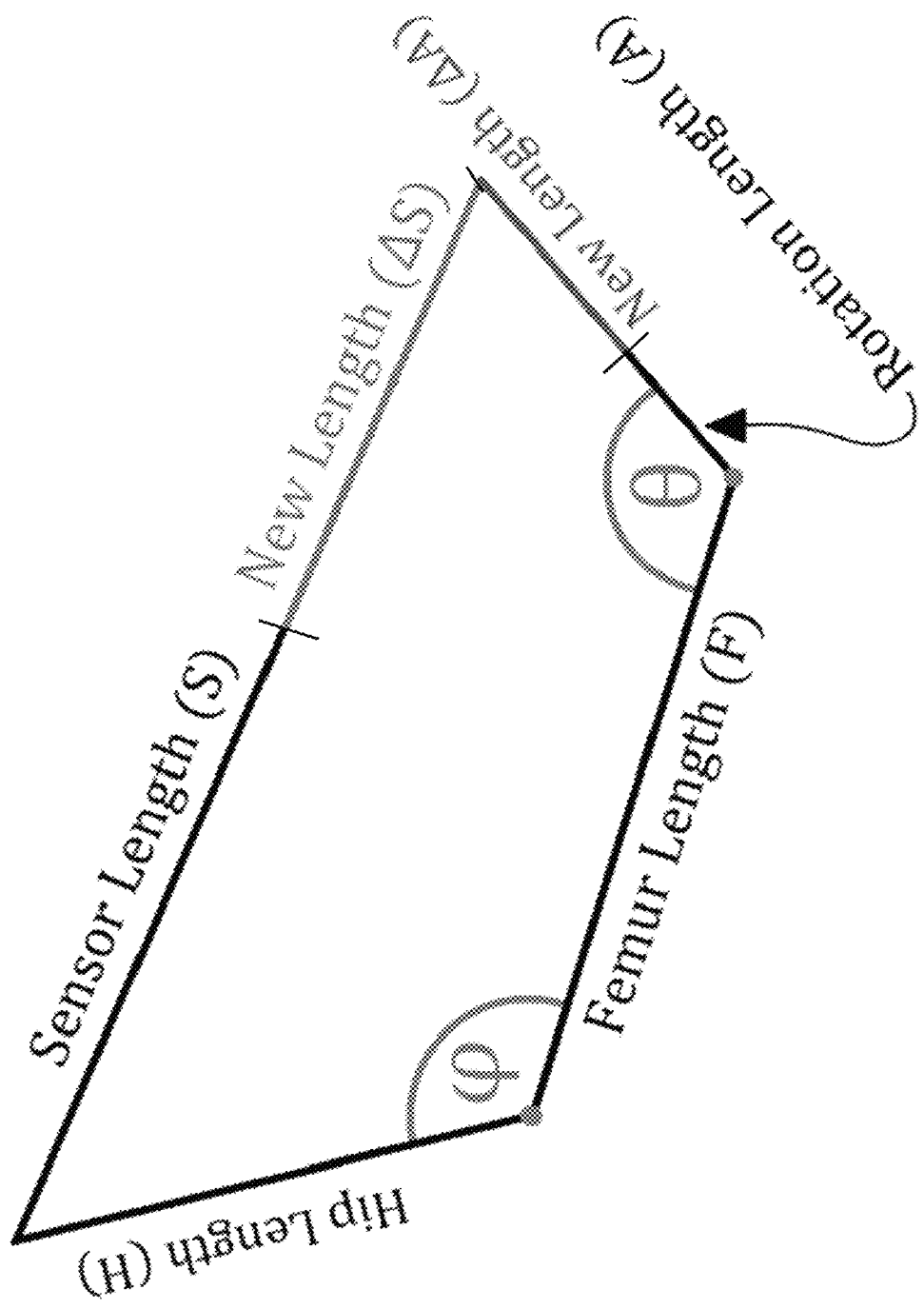
FIG. 7 is a planar explanation of a correct, multiple rigid body rotation sensor setup with one unknown, which uses flexion/abduction sensor data to determine variable angles $\psi$ and $\theta$ in accordance with some embodiments of the present disclosure.

FIG. 7 is a planar explanation of a correct, multiple rigid body rotation sensor setup with one unknown ($\Delta A$), which uses flexion sensor data to determine variable angles $\psi$ and $\theta$. Here again, the hip is used as an example, meaning angle $\psi$ is a multi-dimensional angle.

The CDR and 2CDR sensors' proximal anchors can be attached to more rigid areas that are completely isolated from the rotation, which do not necessarily need to be in a proximal location (the naming will stay the same to highlight the similar function of these anchors and the flexion and rotation sensors' proximal anchors). The 2CDR has the benefit of magnifying the rotational data by anchoring further away from the origin, while also not contacting nor restricting the rigid body being observed. The drawback to both is they rely heavily on other sensors' data, adding to their uncertainty, increasing their potential error, and making their calibration unnecessarily more complex. These sensor variants offer several choices to measure the same value, offering system flexibility to be customized for specific applications and constraints.

The monitors may be useful for accurately quantifying athletic motions to facilitate recovery and/or facilitate form improvement and/or prevent injuries.

A correct rotational sensor arrangement has a single input and only one unknown, which is the measurement of displacement caused by rotation. One equation can be used to solve for one unknown, which is the driving principle behind the configurations of the rotation sensors of the present disclosure. Incorrect arrangements have multiple rigid bodies with multiple unknowns, which describe the bodies' position relative two each other. Any arrangement with a one-dimensional sensor in isolation could not be placed across multiple rigid bodies and produce meaningful data.

For multiple rigid bodies, the same number of sensor inputs are needed, at minimum, to compensate for the degrees of freedom between the bodies to make these dynamic systems solvable. This will inherently increase the uncertainty due to the added number of sensors.

In some embodiments, the monitor is synced to another electronic device (e.g. a phone, a tablet, a laptop, etc.)

Advantageously, no direct line of sight is necessary for monitoring, unlike with camera-based systems. The monitors and methods are also able to track multiple targets without interference, maintaining sensitivity to otherwise discrete motions. The monitors are sufficiently lightweight and passive enough to wear during sporting events without compromising athletic performance. No additional equipment is necessary beyond a computer. The monitors may be integrated into clothing to allow for easy setup.

Although the depicted embodiments are designed for monitoring human legs, other embodiments may be used for monitoring other body parts (e.g. arms, hands, and feet). For example, sensor configuration described herein relative to the knee may also be applicable to the elbow (optionally with modifications). Additionally, the monitors and methods may be used for other species (e.g. in veterinary, zoological, and research applications).

The monitors and methods of the present disclosure may enable real-time flexion and rotation monitoring of limbs. The monitors and methods may be used in laboratory conditions and/or during actual athletic competition.

The monitors may be configured to digitally record and store motion data, allowing for detailed analysis anywhere and at any time.

The monitors and methods of the present disclosure may aid in the identification of improper techniques that can deteriorate health and physical performance.

The monitors provide a lightweight, wearable, reliable, passive human motion capture system that is easy to set up and operate.

The monitors and methods of the present disclosure may be useful for sports medicine, athletic trainers, rehabilitation centers, high schools, universities, private gyms, sports teams (e.g. professional sports teams), and sports equipment.

The monitors or the present disclosure may be used in combination with inertial measurement units (IMUs), stereo-photogrammetric (camera-based) systems, and braces (e.g. knee and leg braces).

The sensors may be analog sensors, digital sensors, or a combination thereof.

Figure 8:
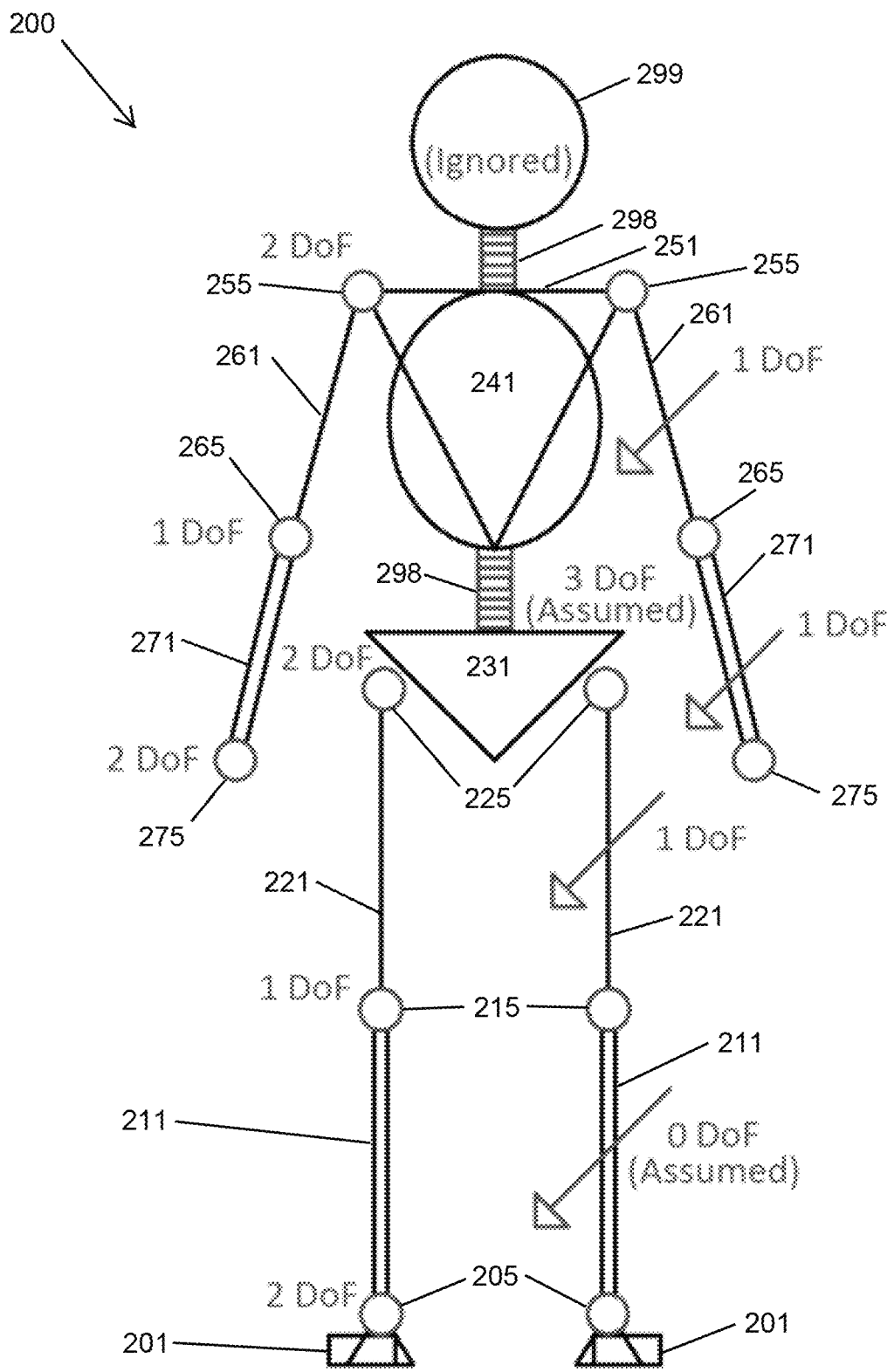
FIG. 8 is a diagram of a human body model.

FIG. 8 illustrates a human body model 200 with associated degrees of freedom (DoF) for various structures thereof. Ankle joints 205 connect feet 201 to lower legs 211. Knee joints 215 connect the lower legs 211 to the upper legs 221. Hip joints 225 connect the upper legs 221 to the pelvis 231. The spine 298 connects the pelvis 231 to the rib cage 241 and the head 299. Should joints 255 connect the collar bones 251, rib cage 241, and upper arms 261. Elbow joints 265 connect the upper arms 261 to the lower arms 271. The lower arms 271 extend between the elbow joints 265 and the wrist joints 275.

Figure 9:
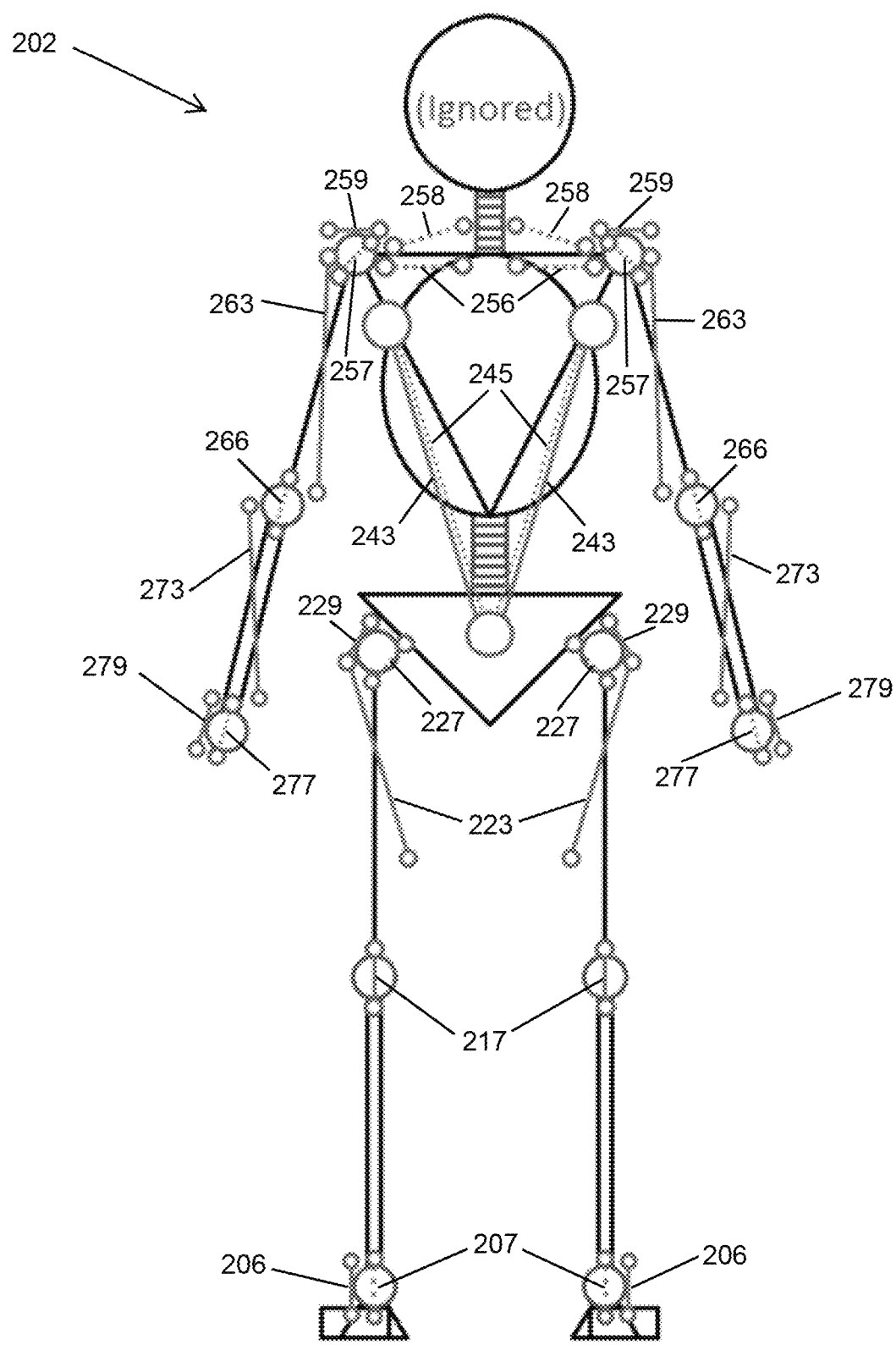
FIG. 9 schematically illustrates a sensor system in accordance with some embodiments of the present disclosure.

FIG. 9 includes a sensor system 202 in accordance with some non-limiting embodiments of the present disclosure applied to the model 200 of FIG. 8. Due to the large number of elements, the reference numerals included in FIG. 8 are omitted from FIG. 9. The sensor system 202 of FIG. 9 may be included in a bodysuit. It should be understood that the sensor systems of the present disclosure may include any combination of the depicted sensors and optionally additional sensors. For example, an upper leg sensor system may be in the form of pants, shorts, or an upper leg sleeve or brace and may only include sensors 217, 223, 227, 229 in some embodiments. It is also contemplated that the sensors system may focus exclusively on one side (e.g. right upper leg or left upper leg). FIG. 9 is a front view wherein solid lines represent sensors visible from the front and dashed lines represent sensors located at the rear. However, it is contemplated that sensors depicted as being located in the front could be moved to the rear and sensors depicted as being located in the rear could be moved to the front. Various sensor locations will depend on the application. For example, some sensor setups may offer enhanced accuracy whereas other sensor setups offer more flexibility.

The depicted sensor system 202 includes ankle abduction sensors 206 and rear ankle sensors 207; knee flexion sensors 217; hip rotation sensors 223, rear hip flexion sensors 227 and hip abduction sensors 229; front upper torso rotation sensors 243 and rear upper torso rotation sensors 245 (these four sensors may monitor the three degrees of freedom of the spine and may be referred to collectively as "the spine motion monitor); shoulder pronation sensors 256, second shoulder flexion sensors 257, shoulder elevation sensors 258, and should abduction sensors 259; shoulder rotation sensors 263; elbow flexion sensors 266; forearm supination sensors 273; and wrist flexion sensors 277 and wrist abduction sensors 279. In some embodiments, sensors 207, 227, and 257 are omitted.

In some embodiments, at least two sensors may share at least one common anchoring point. In other embodiments, not two sensors share a common anchoring point.

Although not depicted, it is also possible to include a rotation sensor on the lower leg. In some embodiments, this sensor is useful for injury identification purposes.

Non-limiting examples of anchor locations include locations at or near various landmarks on the human body including the Anterior Superior Iliac Spine (ASIS), Greater Trochanter of the Femur, epicondyles of the knee and elbow, and the ankle malleolus.

In non-limiting embodiments, sensor data collection/processing includes mechanical strain/stretching elongate the primary sensor, causing its effect on the electrical signal passing through it to change. This altered, analog signal is digitized and converted into strain percentage data through a hardcoded filter. This data is then sent to a computer or embedded system and is plugged into a calibrated set of equations with other relevant sensor signals (processed identically) that correspond to identified pollution sources. This equation produced a joint angle value that reflects the motion produced by the joint being monitored by the primary sensor.

In non-limiting embodiments, the calibration method and equations include equations used to calibrate the signal of the strain sensors from strain to joint angle data is composed of two main parts; the geometric portion and the pollution portion. Both portions of the equation contain variables that correspond to unknown constants, some of which vary depending upon subject proportions and size. The geometric portion of the equation is based off mathematical models that reflect the geometry of the joint being monitored. The constants associated with the geometric portion typically reflect physical dimensions of the body or relate the sensor data to an appropriate length scale, including a zeroing term. The geometric portion uses only the primary sensor that directly monitors the joint motion (the hip flexion sensor is the primary sensor of the hip flexion motion). The pollution portion of the equation is designed to filter out strain information captured by the primary sensor, caused by the complex movements by the surrounding anatomy (including, but not limited to, the flexing of underlying muscles, the complex stretching and pulling of the underlying skin). The pollution portion must contain additional sensor signals to the primary one. The constants associated with the pollution portion reflect a complex array of values and ratios that are difficult to generalize but some are affected by subject sizes and proportions. When these two portions are combined, the equation produces a calibration method that produces a generalized, stable calibration equation that can be tailored to most, if not all, subjects that conform to the physical modelling used to construct the geometric portion.

Calibration methods (e.g. reticulated calibration methods) are also disclosed. In some embodiments, the calibration method uses multiple sensor inputs and produces one output for every unique motion monitored. The methods may rely on physical model-based equations and/or learning software (e.g. neural networks, Gaussian process regression).

Figure 10:
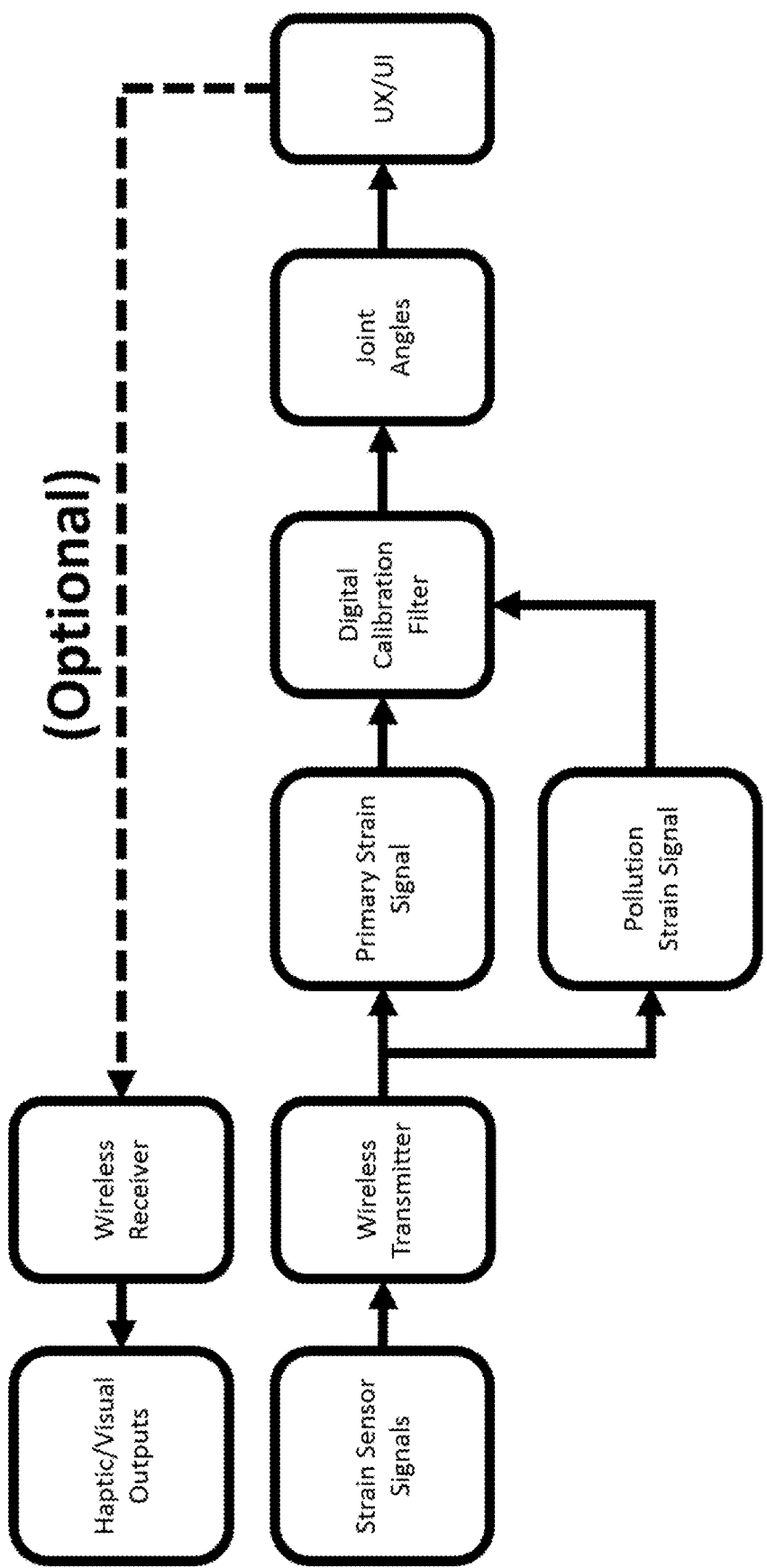
FIG. 10 is a flow chart illustrating a non-limiting embodiment of a method in accordance with some embodiments of the present disclosure.

FIG. 10 is a flow chart illustrating an exemplary method in accordance with some embodiments of the present disclosure. Strain signals generated by the strain sensors may be transmitted (e.g. wirelessly) to a digital calibration filter. The strain signals include a primary strain signal and at least one secondary (pollution) strain signal.

An anterior cruciate ligament (ACL) monitoring system prototype was constructed. The prototype includes a knee flexion sensor, a hip flexion sensor, a hip abduction sensor, and a hip rotation sensor. The hip rotation sensor may be considered the primary sensor and the knee and hip flexion sensors as well as the hip abduction sensor may be considered to be secondary sensors. For example, hip abduction, hip flexion, and knee flexion may create pollution that makes the hip rotation sensor measurement more accurate. The secondary sensors can be used to adjust the estimated rotation from the hip rotation sensor by mitigating the pollution, thereby resulting in a more accurate hip rotation determination.

Adduction/abduction sensors may be of the same type as flexion/extension sensors but rotated (e.g. 90°). It should be understood that for joints capable of flexion/extension and adduction/abduction, an adduction/abduction sensor may be used in addition or as an alternative to any disclosed flexion/extension sensor and vice versa.

Figure 11:
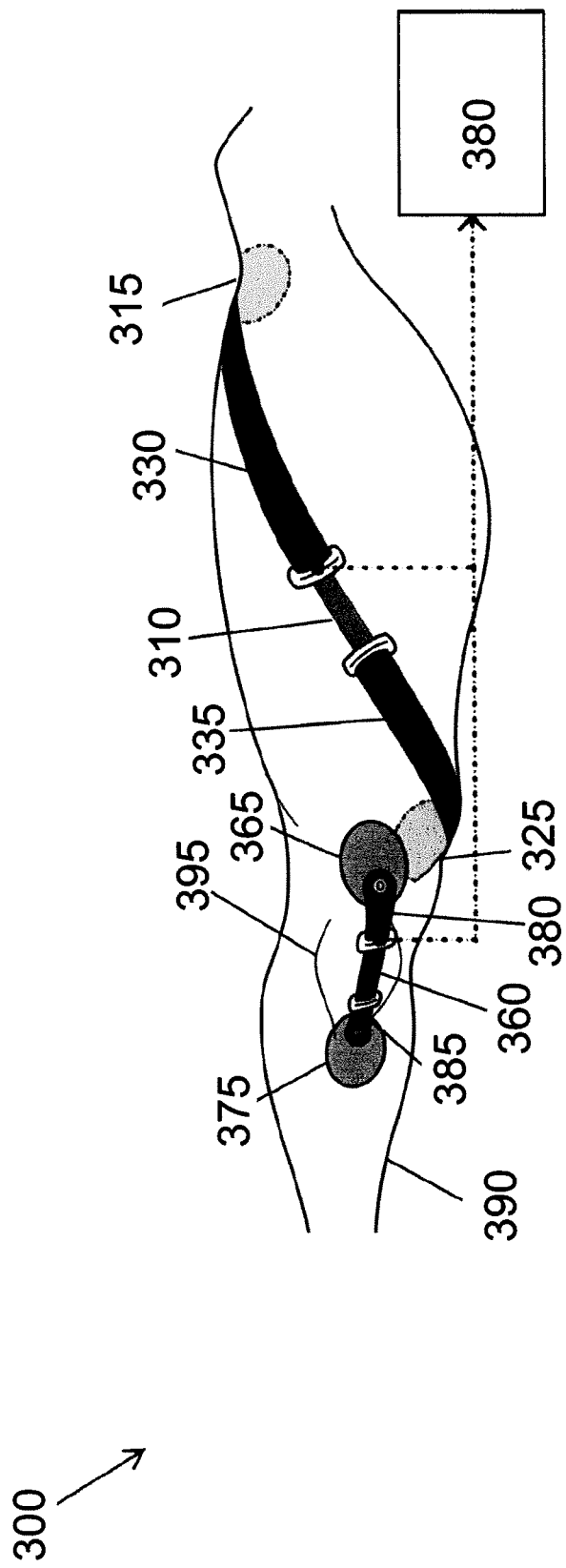
FIG. 11 is a diagram of a sleeve in accordance with some embodiments of the present disclosure.

FIG. 11 is a diagram of a sleeve 300 in accordance with some embodiments of the present disclosure. The sleeve includes both a flexion sensor and a rotation sensor. However, it should be understood that the flexion sensor is omitted in some embodiments. Additionally, more than one rotation sensor and/or more than one flexion sensor may be included in other embodiments. Furthermore, one or more abduction/adduction sensors/monitors may be included in addition or as an alternative to the flexion sensor(s). In the depicted sleeve 300, the flexion and extension monitor 360 is secured to a body part 390 using anchors 365, 375 applied above and below a hinge joint 395. In some embodiments, the anchors 365, 375 are chemically applied (e.g. via an adhesive directly to the skin). In other embodiments, the anchors 365, 375 are mechanically applied. In further embodiments, the anchors 365, 375 may be applied via suction. A first strap 380 may be used to secure the sensor/monitor 360 to the first anchor 365 and a second strap 385 may be used to secure the sensor/monitor 360 to the second anchor 375.

The rotation monitor 310 is also secured to the body part 390 using anchors 315, 325. In the depicted embodiment, the anchors 315, 325 are applied such that the monitor 310 partially wraps around the body part 390. The rotation monitor anchors 315, 325 may have similar or different configurations compared to the flexion monitor anchors 365, 375. The rotation monitor 310 may be secured to the rotation monitor anchors 315, 325 via straps 330, 335.

Sensor measurements (e.g. voltages) are transmitted for data processing 380 (e.g. by a computer including a processor). Data transmission may be wired or wireless. In some embodiments, the data processing 380 is performed in real-time. In other embodiments, data is collected and subsequently processed at a later time. Data processing may be performed on-site or off-site.

Figure 12:
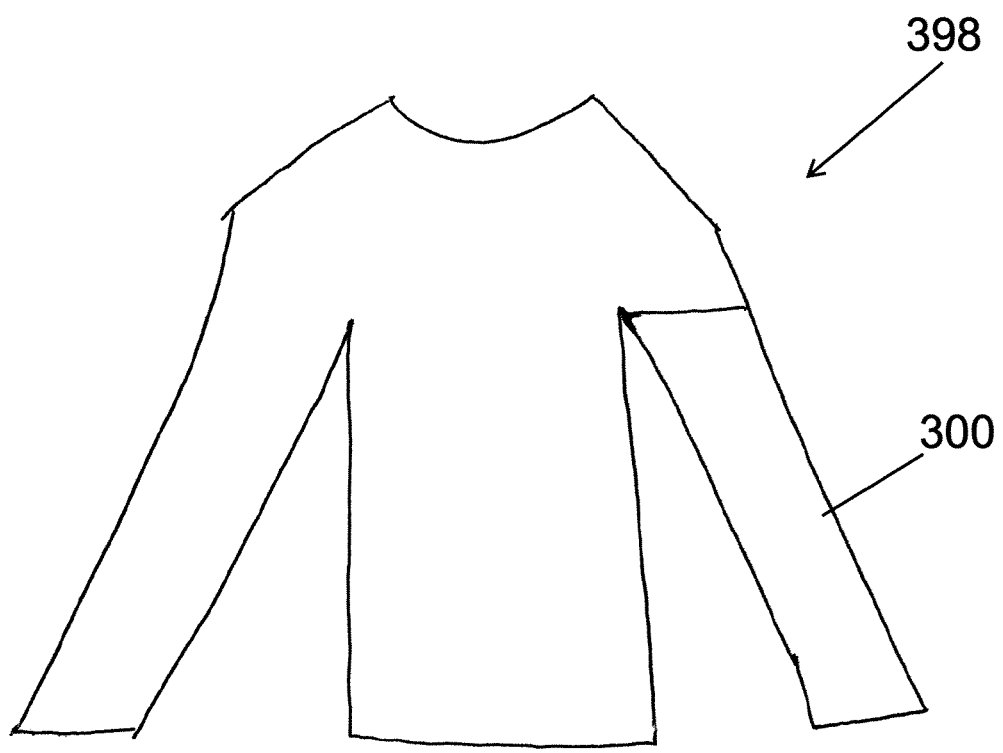
FIG. 12 is a diagram of a shirt including the sleeve of FIG. 11.

FIG. 12 is a diagram of a shirt 398 including the sleeve 300 of FIG. 11.

Figure 13:
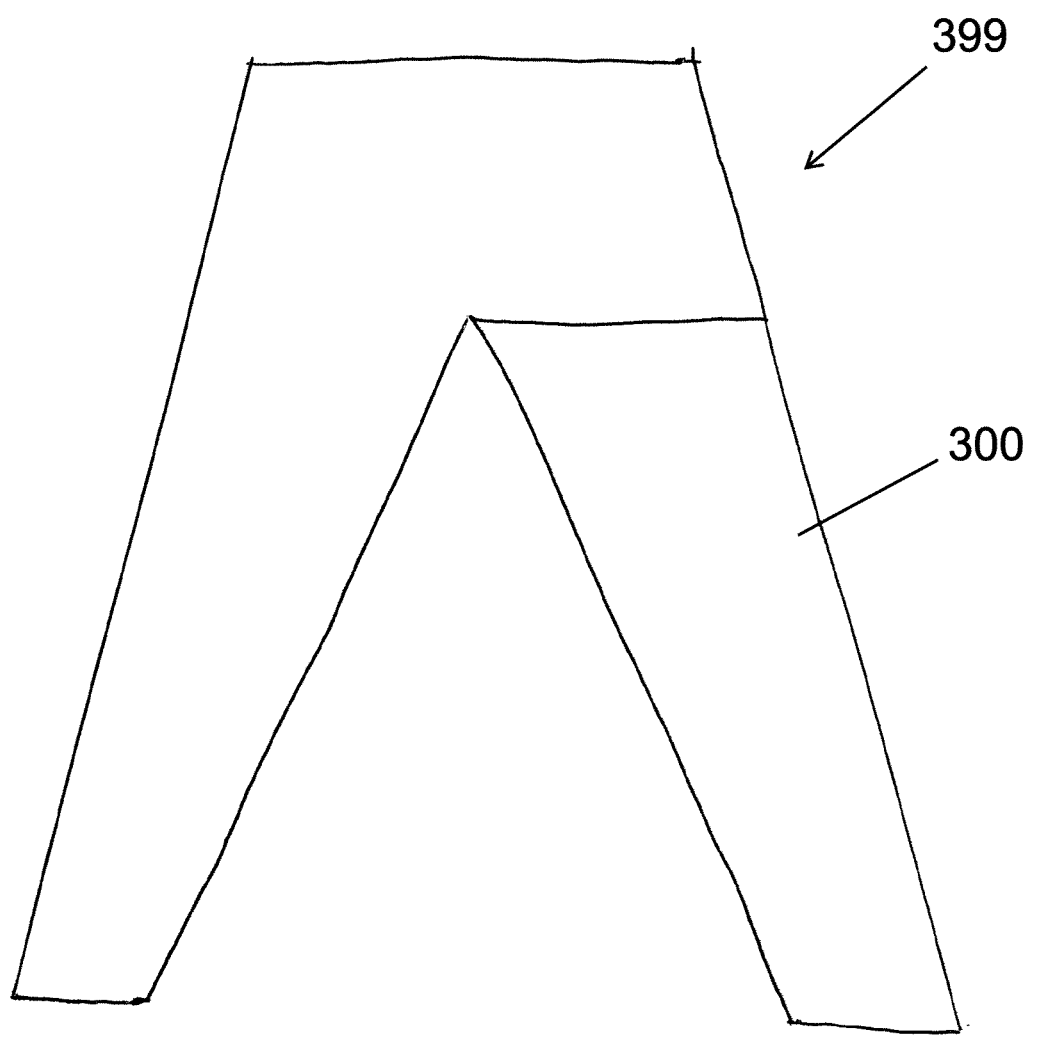
FIG. 13 is a diagram of pants including the sleeve of FIG. 11.

FIG. 13 is a diagram of pants 399 including the sleeve 300 of FIG. 11.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A garment comprising a first system for measuring axial rotational motion of a rigid body, the first system comprising:

a first anchor configured to be anchored at or near a proximal location which originates the rotational motion of a rigid body;

a first strain-monitoring sensor connected to the first anchoring element; and a second anchor connected to the first strain-monitoring sensor and configured to be anchored on a distal location of the rigid body opposite the first anchor;

wherein the first system extends at least partially around an axis of rotation of the rigid body;

wherein both the proximal location and the distal location are located on a lateral face of a body part associated with the rigid body; and wherein the first system is in communication with a computer configured to:

based on a model of the rigid body as a cylinder, wherein a height of the cylinder defines a fixed length of a first non-hypotenuse side of a triangle, an arc defining a portion of a circumference of the cylinder which the first system traverses defines a variable length of a second non-hypotenuse side of the triangle, and a length of the first system defines a variable length of a hypotenuse side of the triangle:

calculate a change in length of the hypotenuse from a measured strain;

calculate a change in length of the second non-hypotenuse side based on the change in length of the hypotenuse and the fixed length of the first non-hypotenuse side; and estimate axial rotational motion of the rigid body based on the change in length of the second non-hypotenuse side.

2. The garment of claim 1, wherein:
the garment is pants;
the rigid body is a femur;
the proximal location is near a hip joint; and
the distal location is near a knee joint.

3. The garment of claim 2, wherein the proximal location is located on an upper area of a thigh; and wherein the distal location is located on a lower area of a thigh.

4. The garment of claim 3, wherein both the proximal location and the distal location are located on a lateral face of the thigh.

5. The garment of claim 1, wherein:
the garment is pants;
the rigid body is a tibia and a fibula;
the proximal location is near a knee joint; and
the distal location is near an ankle joint.

6. The garment of claim 1, wherein:
the garment is a long-sleeve shirt;
the rigid body is a humerus;
the proximal location is near a shoulder joint; and
the distal location is near an elbow joint.

7. The garment of claim 1, wherein:
the garment is a long-sleeve shirt;
the rigid body is a radius and an ulna;
the proximal location is near an elbow joint; and
the distal location is near a wrist joint.

8. The garment of claim 1, further comprising a second system for measuring flexion, the second system comprising:

a third anchor configured to be anchored on a first side of a hinge joint;

a fourth anchor configured to be anchored on a second side of the hinge joint; and a sensor attached to the third anchor and the fourth anchor.

9. The garment of claim 8, wherein the hinge joint is a knee.

10. The garment of claim 8, wherein the hinge joint is an ankle.

11. the garment of claim 1, wherein the first system extends completely around the axis of rotation of the rigid body.

12. A method for measuring axial rotational motion of a limb bone, the method comprising:
  providing a sleeve to a limb, wherein the sleeve comprises a first strain-monitoring sensor extending in a partial helix around an axis of rotation of the limb bone and wherein the first strain-monitoring sensor comprises a first anchor at a proximal location of the limb bone which originates the rotational motion of the limb bone and a second anchor at a distal location of the limb bone opposite the proximal location;
  measuring strain with the first strain-monitoring sensor;
  modeling the limb bone as a cylinder, wherein a height of the cylinder defines a fixed length of a first non-hypotenuse side of a triangle, an arc defining a portion of a circumference of the cylinder which the first strain-monitoring sensor traverses defines a variable length of a second non-hypotenuse side of the triangle, and a length of the first strain-monitoring sensor defines a variable length of a hypotenuse side of the triangle;
  calculating a change in length of the hypotenuse from the measured strain using a computer;
  calculating a change in length of the second non-hypotenuse side based on the change in length of the hypotenuse and the fixed length of the first non-hypotenuse side using the computer; and
  estimating axial rotational motion of the limb bone based on the change in length of the second non-hypotenuse side using the computer.

13. The method of claim 12, wherein the limb bone is selected from the group consisting of: a femur, a humerus, a tibia and a fibula, and a radius and an ulna.

14. The method of claim 12, further comprising:
  assessing an injury risk based on the estimated axial rotational motion.

15. The method of claim 14, wherein the injury is selected from the group consisting of a torn anterior cruciate ligament (ACL), a torn ulnar collateral ligament (UCL), and shin splints.

16. The method of claim 12, wherein the sleeve comprises a high-friction cloth.

17. The method of claim 12, wherein the sleeve comprises a polyamide or a blend of a polyether-polyurea copolymer and cotton.

18. The method of claim 12, further comprising:
  calibrating the sensor using a neural network and/or Gaussian process regression.

19. The method of claim 18, wherein the limb bone is a femur and the sleeve is an upper leg sleeve.

* * * * *